United States Patent [19]

Schinzel et al.

[11] 4,001,130

[45] Jan. 4, 1977

[54] OPTICAL BRIGHTENERS

[75] Inventors: Erich Schinzel, Hofheim, Taunus;
Wilfried Sahm, Kelkheim, Taunus;
Günter Rösch, Altenhain, Taunus,
all of Germany

[73] Assignee: Hoechst Aktiengesellschaft,
Frankfurt am Main, Germany

[22] Filed: Jan. 7, 1974

[21] Appl. No.: 431,045

[30] Foreign Application Priority Data

Jan. 12, 1973 Germany .......................... 2301438

[52] U.S. Cl. ............................. 252/89 B; 252/89 R;
252/135; 252/301.21; 252/301.32; 252/524;
252/543; 260/240 R; 260/240 K

[51] Int. Cl.² ........................................... C11D 3/42

[58] Field of Search ........... 252/89, 80 B, 543, 524,
252/135, 301.3 W, 301.2 W; 260/240 R, 240 K

[56] References Cited

UNITED STATES PATENTS 3,652,284   3/1972   Oliver .......................... 260/240 R

*Primary Examiner*—Mayer Weinblatt
*Attorney, Agent, or Firm*—Connolly and Hutz

[57] ABSTRACT

1,3-Butadienes which are substituted at both terminal carbon atoms with phenyl, naphthyl, theinyl or furyl groups or one benzoxazolyl group are useful as optical brighteners for detergents. The butadienes, some of which are known, can be obtained by HORNER syntheses.

8 Claims, No Drawings

OPTICAL BRIGHTENERS

The present invention relates to butadiene derivatives to be used as optical brighteners for detergents.

From German Pat. No. 1,138,757 it is known that 1,1,4,4-tetraphenyl-butadiene-(1,3) and similar compounds are useful as optical brighteners. An optical brightener to be used in detergents has, however, to meet high requirements: For example, it must easily dispersed in aqueous liquors, it must be compatible with the usual detergent and bleaching components and it must also be stable against those compounds and, above all, it should be absorbed by the conventional substrates from an aqueous liquor at the lowest possible temperature. On the other hand, even upon several washing operations, there must not be any undesired accumulation of the optical brighteners, which would decrease the degree of whiteness or lead to a discoloration.

It has now been found that compounds of the formula (1)

$$A - CH = CH - CH = CH - B \qquad (1)$$

in which A stands for a phenyl, naphthyl, 2-thienyl or 2-furyl group and B for a 2-benzoxazolyl group or for the groups defined sub A, A and B optionally carrying non-chromophorous radicals, are suitable as optical brighteners for detergents.

The present invention provides detergent compositions containing 0.01 to 2% by weight of an optical brightener of formula (1); said composition may contain 99 to 99.98% of a detergent and 0.02 to 1% of said optical brightener.

As non-chromophorous radicals, there are mentioned (preferably lower) alkyl groups, (preferably lower) alkenyl groups, (preferably lower) alkoxy groups; aryl groups, preferably phenyl groups; aralkyl groups, preferably derived from lower alkylene and phenyl groups, such as benzyl and phenylethyl groups; acyl groups, optionally functionally modified carboxy or sulfo groups, acylamino or sulfonyl groups, as well as halogen atoms.

This invention relates to a composition comprising a detergent and an optical brightener of the formula (1)

$$A - CH = CH - CH = CH - B \qquad (1)$$

in which A is phenyl, naphthyl, 2-thienyl or 2-furyl and B is 2-benzoxazolyl or defined as A, which radicals A and B are unsubstituted or substituted by lower alkyl; lower alkoxy; phenyl; lower alkyl substituted by phenyl; halogen; cyano; lower alkanoylamino; benzoylamino; carboxy or sulfo or a group of the formula $$-COOR, -CONR^1R^2, -SO_2OR, -SO_2NR^1R^2,$$
$$-COR^3 \text{ or } SO_2R^4$$

in which R is lower alkyl or phenyl, which radicals R are unsubstituted or substituted by hydroxy, lower alkoxy, lower dialkylamino or lower trialkylammonium; $R^1$ and $R^2$ are hydrogen or lower alkyl or $R^1$ and $R^2$ together with the nitrogen are piperidino or morpholino; $R^3$ is lower alkyl or phenyl and $R^4$ is lower alkyl or phenyl which radicals $R^4$ are unsubstituted or substituted by lower dialkylamino, lower trialkylammonium, lower alkanoylamino or sulfo.

More specifically this invention relates to a composition as defined in the immediately preceding paragraph, wherein the brightener has the formula (1), in which A is phenyl, naphthyl, 2-thienyl or 2-furyl and B is 2-benzoxazolyl or defined as A, which radicals A and B are unsubstituted or substituted by lower alkyl, lower alkoxy, phenyl, chlorine, cyano, carboxy, sulfo, lower carboalkoxy or lower carboalkoxy substituted in the alkyl moiety by di-(lower alkyl)-amino or tri-(lower alkyl)-ammonium methosulfate.

By a functionally modified carboxy group, there is generally understood a carboxylic acid derivative in its widest meaning, i.e. a compound having a carbon atom, three bonds of which are linked to hetero atoms, especially oxygen, nitrogen and sulfur atoms. In a narrower sense of this term, it stands for salts with colorless cations, preferably alkali metal or ammonium ions, furthermore the cyano group, a carboxylic acid ester group or a carboxylic acid amide group. Carboxylic acid ester groups are especially understood to correspond to the general formula COOR, in which R stands for a phenyl group or a lower alkyl group which may be branched, these groups optionally containing further substituents, such as a preferably low-molecular-weight dialkylamino or trialkylammonium group, a hydroxy group or a lower alkoxy group. A carboxylic acid amide group is especially understood to correspond to the formula $CONR^1R^2$, in which $R^1$ and $R^2$ each stands for a hydrogen atom or a lower alkyl group which may be substituted and may form, together with the nitrogen atom, a hydroaromatic ring, especially a piperidino or morpholino group; furthermore acid hydrazides and the analogous thio derivatives.

By a functionally modified sulfo group, there is to be understood in analogy to the above definitions, a radical, the sulfone group of which is linked to a hetero atom, that is to say the salts with colorless cations, preferably alkali metal or ammonium ions, furthermore the sulfonic acid ester group and the sulfonic acid amide group. The sulfonic acid ester group is especially understood to correspond to the formula $SO_2OR$, in which R is defined as above, and the sulfonic acid amide group to correspond to the formula $SO_2NR^1R^2$, in which $R^1$ and $R^2$ are defined as above.

An acyl group is especially understood to correspond to the formula $COR^3$, in which $R^3$ stands for an optionally substituted, preferably lower alkyl or phenyl group, especially an unsubstituted lower alkanoyl group or the benzoyl group. The sulfonyl group is especially understood to correspond to the formula $SO_2R^4$, in which $R^4$ stands for an optionaly substituted lower alkyl or phenyl group, both preferably substituted by a lower dialkylamino, lower trialkylammonium, acylamino or sulfo group.

Some of the compounds used according to the invention are known and can be prepared according to various methods, preferably according to the following methods: According to HORNER, I. a phosphorus compound of the formula (2)

is condensed with an acrolein derivative of the formula (3)

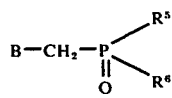

or

II. a phosphorus compound of the formula (4)

is condensed with an acrolein derivative of the formula (5)

OCH—CH CH—A    (5), or

III. a phosphorus compound of the formula (6)

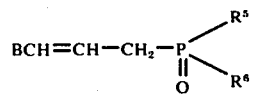

may be reacted with an aldehyde of the formula (7)

OCH - A (7)

or

IV. a phosphorus compound of the formula (8)

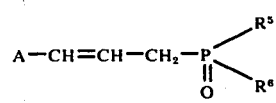

may be reacted with an aldehyde of the formula (9)

B — CHO (9)

The intermediate products (3), (5), (6) and (8) may also be prepared by the HORNER reaction. The two double bonds of the butadiene chain may also be introduced by HORNER reactions by means of a bifunctional component, for example according to the process disclosed in German Pat. No. 1,138,757.

In the formulae (2) to (9), A and B are defined as in the general formula (1). In the formulae (2), (4), (6) and (8), $R^5$ and $R^6$ stand for identical or different alkyl, cycloalkyl, aralkyl or aryl groups which are linked to the phosphorus atom via an oxygen atom. Since the groups $R^5$ and $R^6$ do not appear in the end product, their chemical nature is not critical as regards the product of the invention. For practical reasons, cyclohexyl, benzyl, phenyl and especially lower alkyl groups are, however, preferred.

The above-mentioned methods are advantageously carried out in inert solvents, for example hydrocarbons, such as toluene or xylene, or alcohols, such as methanol, ethanol, isopropanol, butanol, glycol, glycol ethers, such as 2-methoxyethanol, hexanol, cyclohexanol, cyclooctanol; ethers, such as diisopropyl ether, dioxan, tetrahydrofuran; formamides and N-methylpyrrolidone. Especially suitable are dipolar organic solvents, such as dimethylformamide and dimethylsulfoxide.

As condensation agents, there are mentioned strongly basic compounds, for example alkali metal or alkaline earth metal hydroxides, alcoholates or amides, preferably potassium hydroxide, potassium tert.-butylate or sodium methylate, furthermore the alkali metal compounds of dimethylsulfoxide and alkali metal hydrides.

Depending on the kind of starting material used, the reaction temperature is in the range of from about 0° to about 100° C, preferably from about 10° to about 80° C.

The compounds to be used according to the invention are also obtained using, instead of the phosphorus compounds (2), (4), (6) and (8), the corresponding quaternary phosphonium salts, for example the triphenylphosphonium salt, and by condensing them according to WITTIG via the step of the phosphorylenes with the aldehydes (3), (5), (7) and (9).

According to prior art methods for the preparation of 1,4-diaryl butadienes, a condensation of arylacetic acids is carried out with cinnamaldehydes in the presence of acetic anhydride or of β-benzal-propoinic acids with benzaldehydes, lead oxide being advantageously used as a catalyst (cf. Organ. Synth., Coll. Vol. II, 229).

The reaction products obtained according to the invention may further be modified by known methods, for example by sulfonation reactions with sulfonating agents, for example $H_2SO_4$, mixtures of $H_2SO_4$ and $SO_3$, amidosulfonic or chlorosulfonic acid, moreover by reactions which start, for example, from molecules containing sulfo or carboxy groups and yield compounds having functionally modified sulfo or carboxy groups, or by conversions of those groups into other groups of this kind or into the free acids.

Compounds to be used according to the invention are, for example, the following:

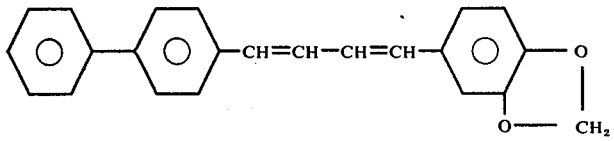

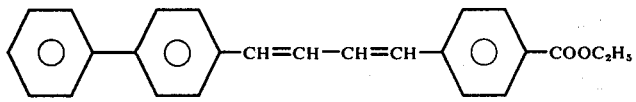

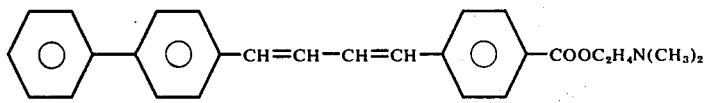

-continued
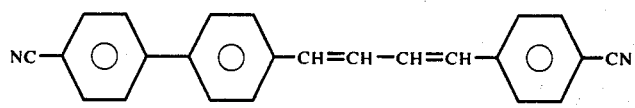
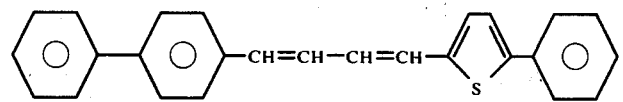
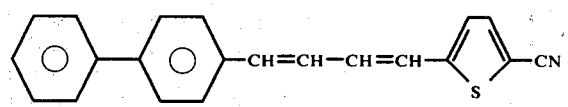
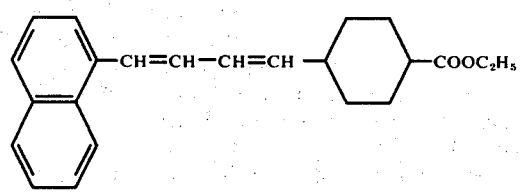
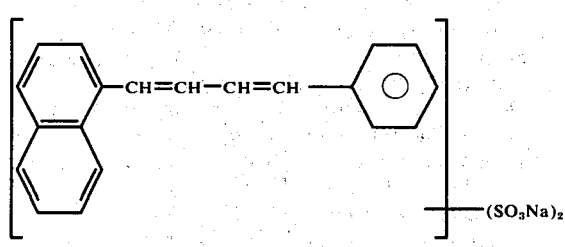
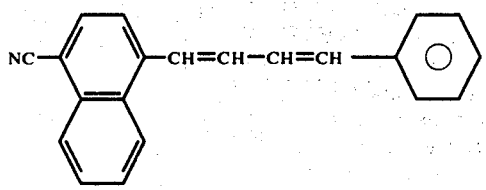
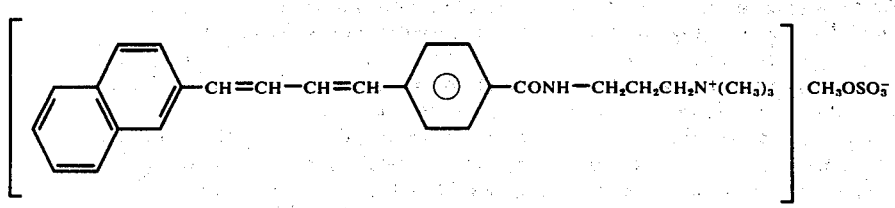
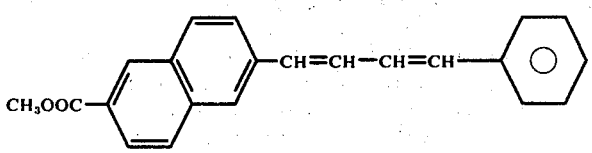
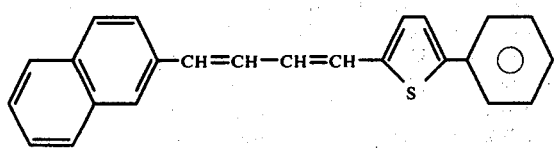

-continued

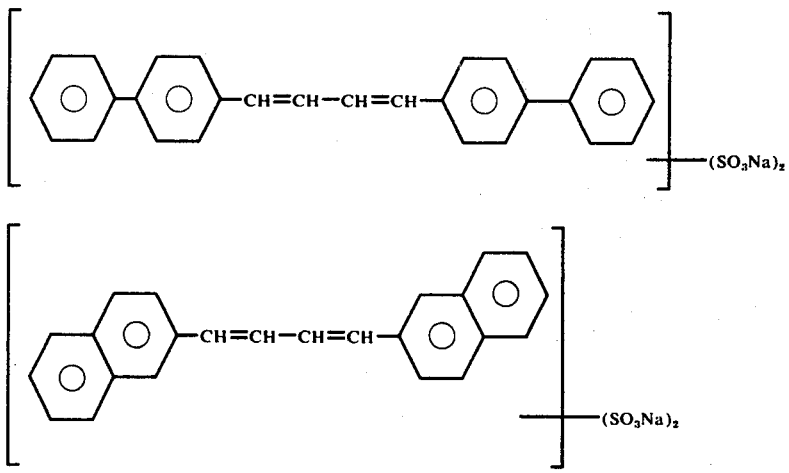

The detergents, in which the compounds of the formula (1) are incorporated according to the invention, may contain the usual fillers and adjuvants, such as alkali metal silicates, alkali metal phosphates or condensed phosphates, alkali metal borates, alkali metal salts of carboxymethyl cellulose, foam stabilizers, such as alkanol-amides of high-molecular-weight fatty acids, or complexing agents, such as soluble salts of ethylene-diamine tetraacetic acid or diethylene-triamine pentaacetic acid, as well as chemical bleaching agents, such as perborates or percarbonates, perborate activators of the polyacetic acid amide type which split off peracetic acid when combined with peroxo compounds, and disinfectants. The detergents which have been prepared using optical brighteners according to the invention may have the compositions usual for products of this type. The portion of the optical brighteners is generally in the range of from about 0.1 to 1% by weight. The other components of such detergents are, above all, surfactants in an amount of from about 5 to 40, preferably 10 to 30% by weight; builders in an amount of from about 10 to 80, preferably 30 to 75% by weight; inorganic peroxo compounds, such as perborates; and perborate activators, for example tetraacetyl-glycoluril and hexaacetyl-triethylene tetramine, in an amount of from about 5 to about 50% by weight altogether, as well as further detergent components and adjuvants, for example anti-redeposition agents, enzymes, dyestuffs, perfumes and water in a total amount of from about 0 to 15, preferably 1 to 10% by weight.

The surfactants may either be uniform products or mixtures on the basis of anionic or nonionic compounds; they may, for example, consist entirely or to a proportion of about 10 to 50% by weight of soap that may be derived from natural or synthetic fatty acids. They may further consist entirely of surface-active compounds of the sulfate or sulfonate type or may contain these compounds in an amount of about 30 to 70%. Products of this type are, for example, alkyl-aryl-sulfonates and aliphatic sulfonates, such as long-chain alkyl-sulfonates, alkenyl-sulfonates or alkoxy-sulfonates; fatty alcohol sulfates and sulfation products of alkoxylated alkyl-phenols, fatty acid amides or fatty acid alkylol amides with a content of about 1 to 20 ethoxy and/or propoxy groups per molecule, as well as sulfated monoglycerides. Anionic surfactants suitable for the use in detergents have been disclosed in detail, for example in "Surface Active Agents and Detergents" by Schwartz, Perry and Berch, Vol. II (1958), pages 25 to 102.

The surfactants of these detergents may either consist entirely of non ionic detergent basic materials or they may contain these materials in an amount of about 5 to 50% by weight. In these products, the water-solubility of the hydrophobic molecule moiety generally containing about 8 to 30 carbon atoms is brought about, in the simplest case, by introducing polyether chains. Those non ionic detergent basic materials have been disclosed, for example, in "Surface Active Agents and Detergents", Vol. II (1958), pages 120 to 143.

In addition to non ionic and anionic detergent basic materials, the surfactant moiety of the detergents may also contain slight amounts of up to about 8% by weight of foam stabilizers or foam inhibitors.

The foaming power of the synthetic anionic or non ionic surfactants may also be reduced by adding soaps. So, certain combinations of synthetic anionic surfactants, nonionic surfactants and soap have their foaming power reduced substantially. The same applies, among other, also to the addition products of propylene oxide on surface-active polyethylene glycol ethers.

Another substantial component of the detergents are the so-called builders. At least part of them should give an alkaline reaction. For the rest, the builders may be inorganic or organic salts which give a weakly acid, neutral or alkaline reaction, especially salts having complexing properties. Useful builders are, for example, alkali metal carbonates or silicates, mono-, di- or tri-alkali metal orthophosphates, di- or tetra-alkali metal pyrophosphates as well as the metaphosphates known as complexing agents; furthermore, water-soluble salts of high-molecular-weight polycarboxylic acids, especially polymers of maleic acid, itaconic acid, mesaconic acid, fumaric acid, aconitic acid and methylene-malonic acid. Copolymers of these acids with one another or with other polymerizable substances, such as ethylene, propylene, acrylic acid, crotonic acid, vinyl acetate, acrylic amide and styrene, are also suitable. AS complex-forming builders, the polyphosphates which give an alkaline reaction, especially tripolyphosphate, are particularly useful. Organic complexing agents to be used as builders are, for example, nitriloacetic acid, ethylene-diamine tetraacetic acid and similar compounds. Suitable inorganic and organic builders have been disclosed, for example, in "Surface Active Agents and Detergents", Vol. II (1958), pages 289 to 317.

The detergents may also contain stabilizers for the peroxo compounds, especially alkaline earth metal silicates, in particular magnesium silicates, or organic complexing agents.

Depending on the intended purpose and on the application conditions, the pH-value of the aqueous liquors of the detergents may range from weakly acid over neutral to alkaline, as desired, and it may be adjusted by adding the corresponding inorganic or organic acids, buffer substances or bases. In the case of detergent liquors, the pH-value will be generally in the range of about 7 to 12, if the detergent is used in a 1% solution. The pH of heavy-duty laundring agents is, in most cases, adjusted to a more alkaline value of about 9.5 to 12. The pH-value of detergents is generally adjusted by means of the builders which give a neutral to alkaline reaction.

Some of the optical brighteners to be used according to the invention are novel compounds. Therefore, some of the following Examples refer to the preparation of representative compounds, the rest may be synthesized by analogous or known methods.

The following Examples serve to illustrate the invention, the parts and percentages being by weight unless stated otherwise.

EXAMPLE 1

1-Phenyl-4-(diphenylyl-4')-butadiene-(1,3) (104)

202.5 g of 1-chloromethyl-diphenyl, 335 ml of triethylphosphite and 500 ml of dimethylformamide were heated while stirring to 120° C. In the course of 4 hours, the internal temperature was raised to 150° C and the ethyl chloride distilling off was condensed in a cooling trap. Subsequently, dimethylformamide and excess triethyl-phosphite were distilled off in a water-jet vacuum.

According to an analysis made by gas chromatography, (in the following: GC), the remaining oily residue (315 g) contained 86% of diphenylyl-(1)-methyl-phosphonic acid diethyl ester.

17.45 g of the above phosphonic acid ester and 6.61 g of cinnamaldehyde were dissolved in 50 ml of dimethylformamide, and at a temperature below 30° C a suspension of 6.17 g of potassium tert.-butylate in 100 ml of dimethylformamide was added. The mixture was stirred for 45 minutes at room temperature, then added to 900 ml of ice water, the pH was adjusted to 5 by means of hydrochloric acid and the precipitate was suction-filtered after about 1 hour. The filter-residue was washed with water until free from chlorine ions and dried in vacuo at 60° C. 14.9 g (99%) of a yellow powder were obtained, which upon recrystallization from chlorobenzene/charcoal had a constant melting point of 205° to 207° C.

In an analogous manner, the compounds (111), (117) and (122) could be prepared using 4-methoxy-cinnamaldehyde, 4-cyano-cinnamaldehyde and 4-phenyl-cinnamaldehyde. The sparingly soluble compound (122) could be recrystallized from dimethylformamide.

EXAMPLE 2

1-Phenyl-4-(α-naphthyl)-butadiene-(1,3) (105)

110.5 g of 1-bromomethyl-naphthalene and 500 ml of triethylphosphite were heated while stirring to 120° C and the temperature was raised to 150° C within the following 4 hours. Ethyl bromide distilling off was condensed in a cooling trap. After distilling off excess triethyl-phosphite 138 g of a faintly yellow oil were obtained which, according to GC, contained 98% of α-naphthyl-methyl-phosphonic acid diethyl ester.

The reaction of this phosphonic acid ester with cinnamaldehyde in the manner indicated in Example 1 provided a 90% yield of the crude product (105) as a yellow powder which upon recrystallization from n-butanol/charcoal had a constant melting point of 108° to 109° C.

Using 4-methoxy-cinnamaldehyde, 4-cyano-cinnamaldehyde, 4-phenyl-cinnamaldehyde and 2-(α-naphthyl)-acrolein, the compounds (112), (118), (123) and (127) were obtained also in good to very good yields.

EXAMPLE 3

1-Phenyl-4-(β-naphthyl)-butadiene-(1,3) (106)

Starting from 2-bromomethyl-naphthalene, the β-naphthylmethyl-phosphonic acid diethyl ester was prepared in a manner analogous to that disclosed in Example 2.

The condensation of this phosphonic acid ester with cinnamaldehyde in dimethylformamide and with potassium tert.-butylate as the condensation agent afforded a 95% of yield of the crude compound (106) in the form of a brownish crystallized powder which could be purified from n-butanol/charcoal Constant melting point: 184–186° C.

The compounds (113), (119), (124), (128) and (131) were obtained by starting from the corresponding substituted cinnamaldehydes, the yields obtained were very good also when, as was the case with p-cyano-cinnamaldehyde, a suspension of ground sodium hydroxide in dimethylformamide was used as a condensation agent.

EXAMPLE 4

1-Phenyl-4-[thienyl-(2')]-butadiene-(1,3) (107)

62.9 g of 2-chloromethyl thiophene and 94.5 g of triethylphosphite were heated while stirring within 4 hours to an internal temperature of 150° C. Excess triethyl phosphite was then distilled off in a water-jet vacuum. 109.8 g of a yellow oil (99% of the theoretical yield) were obtained, which according to GC contained 93.7% of the desired phosphonic acid ester.

7.25 g of the above phosphonic acid ester and 3.96 g of cinnamaldehyde were dissolved in 30 ml of dimethylformamide, and at 30° to 40° C a suspension of 5 g of potassium tert.-butylate in 70 ml of dimethylformamide was added. Stirring was continued for 15 minutes at room temperature, the mixture was poured onto 900 ml of ice water, neutralized with dilute hydrochloric acid and suctionfiltered after about half an hour. The filter residue was washed with water until free from chlorine ions and dried in vacuo at 60° C. 6.12 g (96.2%) of a yellow powder were obtained, which after having been dissolved and precipitated several times from n-butanol had a melting point of about 149° to 151° C.

In an analogous manner, the compounds (114), (120), (125), (129) and (132) were obtained by starting from the corresponding substituted cinnamaldehydes. The β-naphthyl derivative (132) was purified from chlorobenzene.

EXAMPLE 5

1-Phenyl-4-[benzoxazolyl-(2')]-butadiene-(1,3) (108)

83.8 g of 2-chloromethyl-benzoxazole and 500 ml of triethylphosphite were heated while stirring to 120° C and the temperature was raised to 150° C in the course of 4 hours. Subsequently, excess triethyl-phosphite was distilled off in a water-jet vacuum. 143 g of an oily residue were obtained, which according to GC contained 87.4% of the desired ester. 15.4 g of the above phosphonic acid ester and 6.61 g of cinnamaldehyde were dissolved in 50 ml of dimethylformamide and at a temperature of 30° C a suspension of 6.17 g of potassium tert.-butylate in 100 ml of dimethylformamide was added in the course of 5 minutes. Stirring was continued for 45 minutes at room temperature, the mixture was poured onto 900 ml of ice water, the pH was adjusted to 5 by means of dilute hydrochloric acid, the precipitate was suction-filtered after 1 hour and washed until free from chlorine ions. After drying at 60° C in vacuo, 9.91 g of a brownish powder (80% of the theoretical yield) were obtained, which after having been recrystallized several times from isopropanol had a melting point of 108° to 110° C.

In an analogous manner, the compounds (115), (121), (126), (130) and (133) were obtained by starting from the corresponding substituted cinnamaldehydes. The following Table shows optical brighteners to be used according to the invention and obtained according to the above-mentioned and analogous methods:

| No. | A | B | m.p. ° C | solvent used for purification | λmax Abs.** |
|---|---|---|---|---|---|
| 101 |  |  | 151–153 | n-butanol | 333 |
| 102 | " | 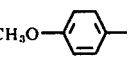 | 159–160 | n-butanol | 342 |
| 103 | " | 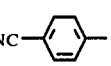 | 165–167 | n-butanol | 348 |
| 104 | " | 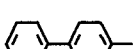 | 205–207 | chlorobenzene | 352 |
| 105 | " | 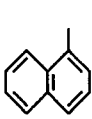 | 108–109 | n-butanol | 359 |
| 106 | " |  | 184–186 | n-butanol | 345 |
| 107 | " |  | 149–151 | n-butanol | 348 |
| 108 | " | 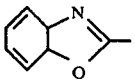 | 108–110 | isopropanol | 350 |
| 109 | 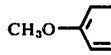 | 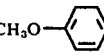 | 224–226 | chlorobenzene | 348 |
| 110 | " | 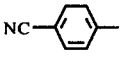 | 173–175* | n-butanol | 361 |
| 111 | " | 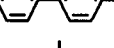 | 230–232* | chlorobenzene | 359 |
| 112 | " |  | 151–153 | n-butanol | 366 |
| 113 | " |  | 199–200* | n-butanol | 353 |
| 114 | " |  | 159–160 | n-butanol | 356 |
| 115 | " |  | 128–129 | isopropanol | 365 |

-continued

| No. | A | B | m.p. °C | solvent used for purification | λmax Abs.** |
|---|---|---|---|---|---|
| 116 | 4-NC-C₆H₄- | 4-NC-C₆H₄- | 263–265 | DMF | 357 |
| 117 | 3-NC-C₆H₄- | 4-biphenylyl | 198–199* | chlorobenzene | 367 |
| 118 | " | 1-methylnaphthalen-yl | 180–182 | n-butanol | 372 |
| 119 | " | 2-methylnaphthalen-yl | 210–213 | n-butanol | 362 |
| 120 | " | 2-methylthienyl | 173–174 | n-butanol | 364 |
| 121 | " | benzoxazol-2-yl | 225–227 | n-butanol | 357 |
| 122 | 4-biphenylyl | 4-biphenylyl | 296–298* | DMF | 368 |
| 123 | " | 1-methylnaphthalen-yl | 143–145 | n-butanol | 368 |
| 124 | " | 2-methylnaphthalen-yl | 251–253 | DMF | 364 |
| 125 | " | 2-methylthienyl | 192–195 | chlorobenzene | 368 |
| 126 | " | benzoxazol-2-yl | 170–172 | n-butanol | 367 |
| 127 | 1-methylnaphthalen-yl | 1-methylnaphthalen-yl | 144–147 | n-butanol | 364 |
| 128 | " | 2-methylnaphthalen-yl | 180–182 | chlorobenzene | 370 |
| 129 | " | 2-methylthienyl | 123–124 | n-butanol | 372 |
| 130 | " | benzoxazol-2-yl | 141–143 | methanol | 374 |
| 131 | 2-methylnaphthalen-yl | 2-methylnaphthalen-yl | 270–271 | DMF | 359 |
| 132 | " | 2-methylthienyl | 198–199 | chlorobenzene | 359 |
| 133 | " | benzoxazol-2-yl | 168–169 | isopropanol | 364 |

\* formed "liquid crystals"
\*\* measured in dimethylformamide (DMF)

EXAMPLE 6

A fabric made of polyamide 6 was treated at a goods-to-liquor ratio of 1:20 with a detergent liquor containing 6 g/l of a detergent of the following composition:

9.8% of isotridecanol-polyglycol ether having, on an average,
8 ethylene glycol units per mol of isotridecanol,
30.0% of sodium tripolyphosphate,
15.0% of tetrasodium pyrophosphate,
5.0% of sodium metasilicate, 2.0% of carboxymethyl cellulose (viscosity of a 2% aqueous solution according to Hoppler at 20° C: 1500 cP) and 0.05% of one of the following optical brighteners, the balance being sodium sulfate.

The fabric was washed for 10 minutes at 60° C and then rinsed and dried as usual. This treatment was repeated up to 10 times. After 1 and 10 operations, respectively, the polyamide fabrics exhibited the following degrees of whiteness according to Berger:

|  |  | 1 washing operation | 10 washing operations |
|---|---|---|---|
| Compound | (108) | 101 | 125 |
|  | (114) | 112 | 134 |

EXAMPLE 7

A knit fabric made of polyamide 6 was treated for 10 minutes at 60° C at a goods-to-liquor ratio of 1:20 in a detergent liquor containing 5 g/l of a detergent of the following composition. The knit fabric was then rinsed and dried. This operation was repeated 10 times. The knit fabric showed a very good degree of whiteness and a substantial increase in whiteness as compared to untreated material.

Composition of the detergent (in percent by weight):
10% of polyglycol ether obtained from technical-grade isotridecanol and, on an average, 8 mols of ethylene oxide,
40% of sodium tripolyphosphate,
1% of technical-grade fatty alcohol ($C_{16}/C_{18}$),
10% of sodium metasilicate,
3% of carboxymethyl cellulose (viscosity of a 2% aqueous solution according to Hoppler at 20° C : 1500 cP),
12% of nonylphenol-polyglycol ether having, on an average, 10 ethylene glycol units, and
0.05% of an optical brightener, the balance being sodium sulfate and a bit of water.

| Degree of whiteness according to Berger | | |
|---|---|---|
| Optical brightener | one washing operation | 10 washing operations |
| 105 | 110 | 134 |
| 109 | 91 | 116 |
| 111 | 94 | 102 |
| 123 | 118 | 140 |
| 124 | 100 | 133 |
| 127 | 90 | 106 |
| 128 | 119 | 138 |
| 131 | 92 | 116 | degree of whiteness of untreated material: 67

We claim:
1. A detergent composition consisting essentially of as optical brightener 0.01 to 2% by weight of a compound of the formula (1)

$$A - CH = CH - CH = CH - B \qquad (1)$$

in which A is phenyl, naphthyl or 2-thienyl and B is 2-benzoxazolyl or defined as A, which radicals A and B are unsubstituted or substituted by lower alkyl; lower alkoxy; phenyl; lower alkyl substituted by phenyl; chlorine; cyano; lower alkanoylamino; benzoylamino; carboxy or sulfo or a group of the formula $$-COOR, -CONR^1R^2, -SO_2OR, -SO_2NR^1R^2,$$
$$-COR^3 \text{ or } SO_2R^4$$

in which R is lower alkyl or phenyl, which radicals R are unsubstituted or substituted by hydroxy, lower alkoxy, lower dialkylamino or lower trialkylammonium; $R^1$ and $R^2$ are hydrogen or lower alkyl or $R^1$ and $R^2$ together with the nitrogen are piperidino or morpholino; $R^3$ is lower alkyl or phenyl and $R^4$ is lower alkyl or phenyl which racicals $R^4$ are unsubstituted or substituted by lower dialkylamino, lower trialkylammonium, lower alkanoylamino or sulfo.

2. A composition as defined in claim 1, consisting of 99 to 99.98% of a detergent and 0.02 to 1% of said brightener.

3. A composition as defined in claim 1, wherein the brightener has the formula 1, in which A is phenyl, naphthyl or 2-thienyl and B is 2-benzoxazolyl or defined as A, which radicals A and B are unsubstituted or substituted by lower alkyl, lower alkoxy, phenyl, chlorine, cyano, carboxy, sulfo, lower carboalkoxy or lower carboalkoxy substituted in the alkyl moiety by di-(lower alkyl)-amino or tri-(lower alkyl)-ammonium methosulfate.

4. A composition as defined in claim 1, wherein the brightener has the formula 1, in which A is phenyl, naphthyl, 2-thienyl, lower alkoxyphenyl, cyanophenyl or biphenylyl and B is 2-benzoxazolyl or defined as A.

5. A composition as defined in claim 1, wherein the brightener has the formula 1, in which A and B are biphenylyl or naphthyl.

6. A composition as defined in claim 1, wherein the brightener has the formula 1, in which A is 1-naphthyl and B is 1-naphthyl, 2-naphthyl or p-biphenylyl.

7. A composition as defined in claim 1, wherein the brightener has the formula 1, in which A is 2-naphthyl and B is 1-naphthyl, 2-naphthyl or p-biphenylyl.

8. A composition as defined in claim 1, wherein the birghtener is 1-(1'-naphthyl)-4-(2'-naphthyl)-butadiene-(1,3).

* * * * *